United States Patent [19]

Reilly

[11] Patent Number: 4,573,978

[45] Date of Patent: Mar. 4, 1986

[54] ANGIOGRAPHIC SYRINGE AND CONNECTOR FOR JOINING A CATHETER THERETO

[75] Inventor: David M. Reilly, Glenshaw, Pa.

[73] Assignee: Medrad, Inc., Pittsburgh, Pa.

[21] Appl. No.: 680,407

[22] Filed: Mar. 15, 1984

[51] Int. Cl.⁴ ............................................ A61M 5/325
[52] U.S. Cl. ...................................... 604/240; 604/283
[58] Field of Search ............... 604/240, 241, 280, 283, 604/905; 285/122, 332, 328

[56] References Cited

U.S. PATENT DOCUMENTS

| 3,601,151 | 8/1971 | Winnard . | |
| 3,684,321 | 8/1972 | Hundhausen et al. . | |
| 3,785,683 | 1/1974 | Adelhed | 604/280 X |
| 4,187,848 | 2/1980 | Taylor | 604/280 |
| 4,254,773 | 3/1981 | Waldbillig | 604/283 |

FOREIGN PATENT DOCUMENTS 2369471  5/1978  France .

Primary Examiner—John D. Yasko
Attorney, Agent, or Firm—Fleit, Jacobson, Cohn & Price

[57] ABSTRACT

An angiographic syringe and a connector for effecting the connection of a catheter to the syringe is disclosed. The connector is a tubular member that engages the syringe at the discharge end and removably engages a suitable end member of a catheter. In the preferred embodiment, the connector is a hollow single-piece structure with tabs at one end for engaging the discharge end of the syringe. A track in the discharge end permits purely rotational movement of the connector about the syringe and eliminates any translational movement thereon. The other end of the connector employs an inner thread to engage the corresponding end of the catheter. Rotational movement of the connector about the discharge end of the syringe draws the catheter into tight engagement therewith, eliminating any rotational movement of either the syringe or catheter.

17 Claims, 5 Drawing Figures 3,573,978

ANGIOGRAPHIC SYRINGE AND CONNECTOR FOR JOINING A CATHETER THERETO

BACKGROUND OF THE INVENTION

1. Field of the Invention

This invention relates to syringes utilized for introducing fluids into the body of a human or an animal, and more particularly to a syringe incorporating a connector which facilitates the interconnection of the syringe with a catheter for rapid and secure interconnection thereof.

2. Background of the Prior Art

In the course of angiographic procedures involving the introduction of radiopaque substances into blood vessels and the like in order to permit diagnostic evaluation of the condition thereof, the radiopaque substance is provided within a syringe and is introduced into the blood stream of the patient in a controlled manner through a catheter which interconnects the vascular system with the syringe. In normal use, the catheter is inserted into the proper blood vessel and the opposite end thereof is connected to the syringe containing the radiopaque substance, the interconnection being accomplished by a threaded connector having means to engage the end of the catheter and an internal thread to engage the discharge opening of the syringe. The connector serves to secure the interconnection in order to preclude separation when pressure is applied to cause the radiopaque substance to flow through the syringe discharge opening and into the catheter for subsequent entry into a blood vessel.

Typically, the catheter has a suitably formed end, opposite the end which is introduced into the blood vessel, and the connector includes a slotted engaging portion into which the catheter end is radially inserted until it is in axial alignment with the connector, whereupon the syringe is threadly engaged with the other end of the connector to effect the connection. Both the catheter end and the syringe discharge opening include cooperatively engageable means to provide a fluid-tight interconnection therebetween, the latter being most often effected by use of a luer taper wherein the catheter end includes an internal luer taper and the syringe discharge opening includes a complementary external luer taper which engages the catheter end and is secured thereto by means of the connector.

The prior art connectors, however, are inconvenient and cumbersome to use in that a relatively large number of rotations of the connector are required in order to effect engagement between the catheter end and the syringe discharge opening. Even if relatively coarse threads are provided, excessive twisting still is required to effect sealing engagement. Additionally, the interconnection normally is accomplished by rotating either the catheter end or the syringe, thereby resulting in an undesirable condition in that the catheter, having once been inserted into the patient, could not be rotated. Further, it is difficult to rotate the syringe because it is held in an angiographic apparatus for controlled injection of the fluid.

SUMMARY OF THE INVENTION

It is an object of the present invention to provide an interconnection means between a syringe and a catheter whereby rapid connection therebetween can be effected.

It is another object of the present invention to provide an interconnection between a syringe and catheter wherein the interconnection is effected in such a manner that the parts thereof are interengaged in fluid-tight relationship.

It is a further object of the present invention to provide an interconnection between a syringe and catheter, wherein the connector rotates rather than translates on the discharge extension of the syringe.

Briefly stated, in accordance with one aspect of the present invention, a syringe is provided and is connectable with a catheter. The syringe includes an elongated tubular body, an intermediate portion and a discharge extension having a discharge outlet at one end and a piston slidably positioned in the tubular body in fluid-tight relationship therewith to control the discharge of fluid through the discharge outlet. The discharge extension of the syringe includes engagement means for permitting engagement of a connector. The connector includes first attachment means cooperable with the engagement means for attaching the connector to the syringe discharge extension in axial engagement with the outlet therein, and second attachment means for cooperatively engaging with a catheter end. The first attachment means is axially spaced from the second attachment means, the former including tabs for engaging with a track in the discharge extension and the latter preferably including a multiple start thread to permit rapid interengagement of the catheter end with the connector member.

DESCRIPTION OF THE PREFERRED EMBODIMENTS

Figure 1:
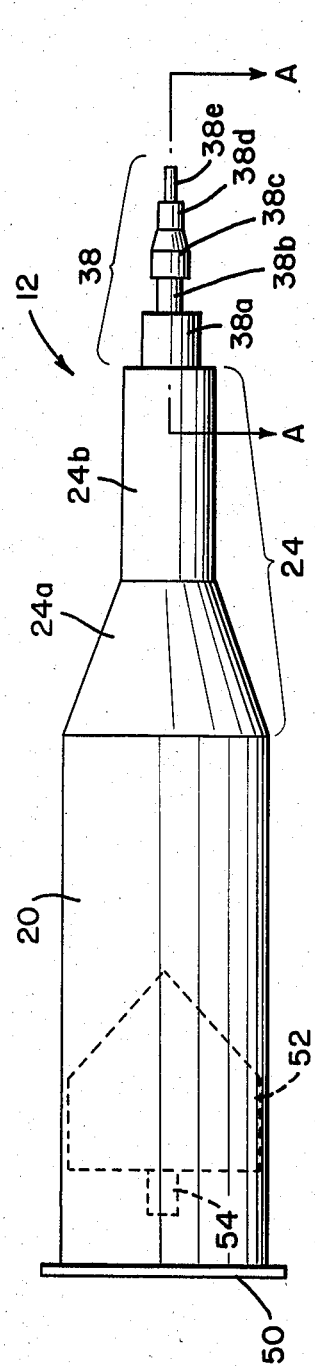
FIG. 1 is a plan view of the syringe of the present invention.
Figure 2:
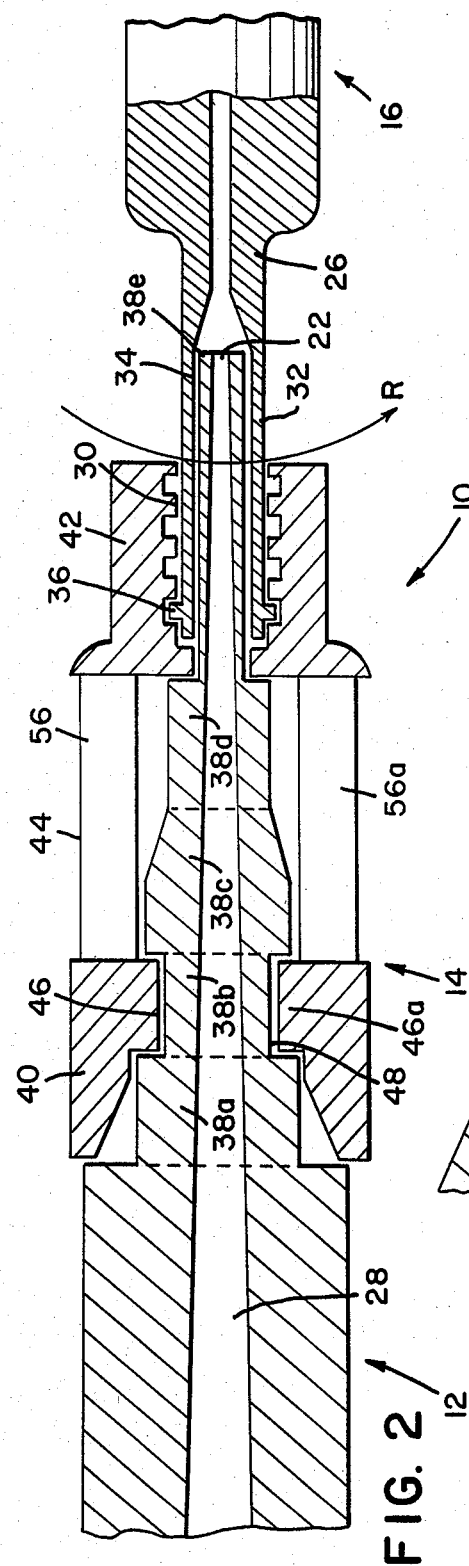
FIG. 2 is a transverse cross-sectional view taken along line A—A of FIG. 1 and line B—B of FIG. 4, showing the operational relationship between the syringe and connector of the present invention.

Referring now to FIGS. 1 and 2, there is shown a syringe-catheter assembly, designated generally by the numeral 10, which utilizes the syringe 12 and connector 14 of the present invention.

The syringe 12 comprises an elongated tubular body 20 and a coaxial discharge extension 38, connected by an intermediate portion 24. The tubular body 20 has a circular, outwardly extending flange 50 on one end, as well as a piston 52 slideably positioned within the tubular body 20. Piston 52 is designed to permit fluid contained within syringe 12 to be dispensed therefrom in a desired quantity and at a desired rate. A suitable rod 54, or the like, can be attached to piston 52 to facilitate axial movement thereof.

Intermediate portion 24 of syringe 12 is in the shape of a funnel and comprises two sections, a hollow cone 24a and a tapered neck 24b. Extending axially from the tapered neck 24b is discharge extension 38 which comprises several portions 38a, 38b, 38c, 38d, and 38e and terminates in discharge outlet 22. Discharge extension 38 serves as a guide means and provides an attachment point for the connector 14. The configuration of the nozzle portion 38e of discharge extension 38 corresponds with generally accepted taper lengths and angles as described in ASA Standard Z-1955 so as to be mateable with conventional catheters 16. Inner passageway 28 within extension 38 can be generally cylindrical, and provides communication between discharge outlet 22 and the interior of tubular body 20.

Engaged with the nozzle portion 38e of discharge extension 38 and enclosing discharge outlet 22 is an end member 26 of a tubular catheter 16, the opposite end of which (not shown) is adapted to be inserted into a blood vessel of a patient. Surrounding the discharge extension 38 and end member 26 of catheter 16 is a connector 14 in accordance with the present invention.

Figure 3:
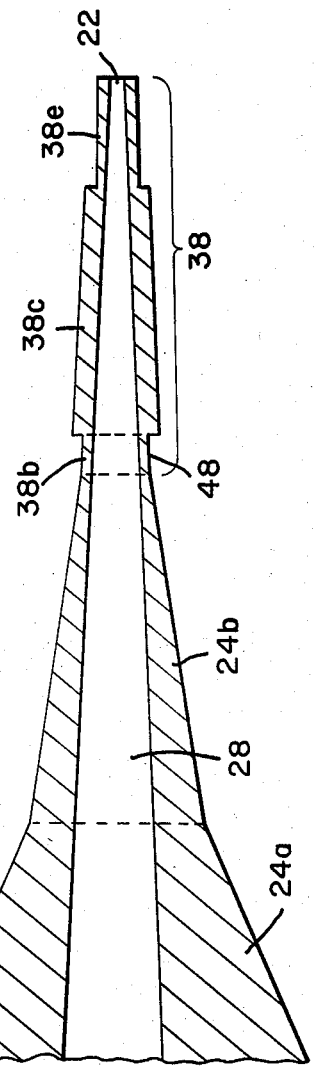
FIG. 3 is a cross-sectional view of an alternate embodiment of the syringe of the present invention.

FIG. 3 illustrates an alternate embodiment of the syringe 12 of the present invention. In this embodiment, discharge extension 38 comprises notched portion 38b, guide portion 38c and nozzle 38e. As in the preferred embodiment, tapered neck 24b extends to the beginning of discharge extension 38; but, unlike the preferred embodiment, tapered neck 24b ends at notched portion 38b where track 48 is located. With both first step 38a and extender portion 38d being eliminated, the remaining portions 38b, 38c and 38e function as in the preferred embodiment. In both embodiments, syringe 12 preferably is formed from a relatively rigid, translucent plastic material.

Referring once again to FIG. 2, catheter end member 26 is seen to include coaxial extension 32, the inner surface 34 of which is formed in a standard luer taper in order to provide a complementary mating surface with the tapered outer surface of nozzle portion 38e. At the end of coaxial extension 32 are a pair of oppositely disposed, outwardly extending edges 36 to faciliate engagement with connector 14.

Figure 4:
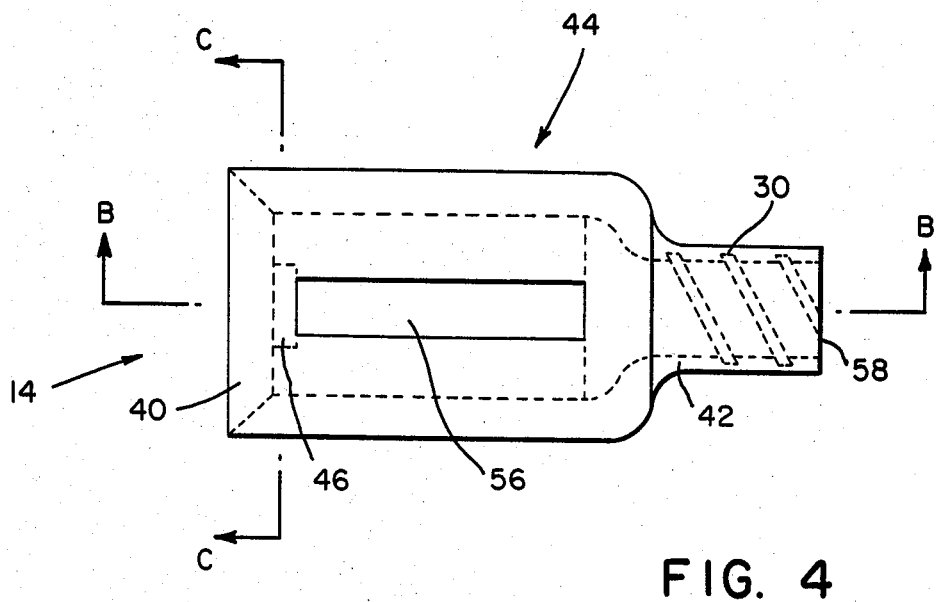
FIG. 4 is a side view of the connector of the present invention.
Figure 5:
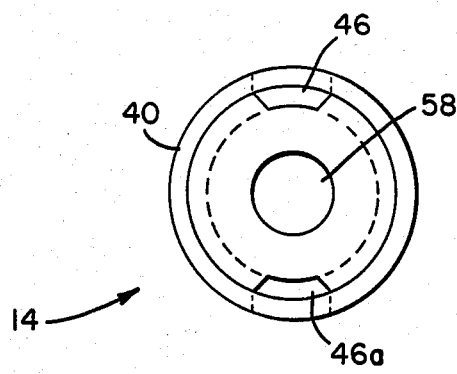
FIG. 5 is a transverse cross-sectional view taken along line C—C of FIG. 4.

Connector 14, which surrounds the interconnection between catheter end member 26 and nozzle portion 38e is shown in FIGS. 2, 4, and 5 to have a generally hollow tubular body, which, as is clearly shown in FIG. 2, is of integral one-piece construction. Positioned internally on the first connector end 40 and integrally formed therewith is attachment means comprising first and second tabs 46 and 46a, disposed opposite one another, which engage track 48 on notched portion 38b of syringe discharge extension 38. Adjacent tabs 46 and 46a are connector windows 56, 56a which run across intermediate portion 44 of connector 14 and simply comprise openings in intermediate portion 44. As such, windows 56, 56a function to make intermediate portion 44 more plyable, thereby allowing tabs 46, 46a to pass over guide extension 38c more easily and facilitating the handling and use of connector 14.

The second end 42 of connector 14 is smaller in diameter than the remainder of the body (which comprises first end 40 and intermediate portion 44) of connector 14 and extends around part of nozzle portion 38e of discharge extension 38, nozzle portion 38e protruding through end opening 58 of connector 14. Positioned internally on second connector end 42 and integrally formed therewith is attachment means comprising a multiple start thread 30 which engages with outwardly extending edges 36 of catheter coaxial extension 32.

In operation, and referring now to the arrangement shown in FIG. 2, connector 14 is slipped into place on syringe 12 by pushing connector 14 over discharge extension 38 in the direction of tapered neck 24b. In the preferred embodiment, tabs 46, 46a will brush across the surface of extender portion 38d being gradually pushed apart as connector 14 passes over the conical guide portion 38c of discharge extension 38. When tabs 46, 46a reach notched portion 38b, they will snap into place in track 48, the first end 40 of connector 14 extending over first step 38a of discharge extension 38. Connector 14 is similarly attached to the syringe shown in FIG. 3. Thus, tabs 46, 46a will be pushed apart as connector 14 passes over guide portion 38c, finally snapping into place in track 48. Once in this position, connector 14 may be rotated about discharge extension 38 while avoiding any translational movement thereon.

After the syringe-connector assembly is complete, catheter 16 may be engaged with syringe 12 as follows. First, coaxial extension 32 of catheter end member 26 is slipped over nozzle portion 38e of discharge extension 38 to the point where outwardly extending edges 36 of catheter 16 engage with the inner threads 30 of connector 14. Connector 14 is then rotated clockwise in the direction of arrow R, tabs 46 and 46a rotating solely within the track 48 of notched portion 38b, thereby causing outwardly extending edge 36 of coaxial extension 32 to become threadly engaged with inner threads 30 of connector 14. This movement draws catheter end member 26 axially along nozzle 38e in a direction toward syringe 12 so as to provide a sealed engagement between the tapered inner surface 34 of the coaxial extension 32 and the corresponding tapered surface of the nozzle portion 38e of the discharge extension 38. It should be noted that the lengths of each of the respective tapers must be sufficiently long so that syringe discharge outlet 22 does not bottom against catheter end member 26 before the inner and outer tapered surfaces com into tight engagement.

By utilizing this arrangement, rotation of either syringe 12 or catheter 16 is eliminated, thereby providing an element of ease in the use of the angiographic injector and eliminating what previously has been a troublesome shortcoming of prior art connectors.

Although a particular embodiment of the present invention has been illustrated and described, it will be apparent to those skilled in the art that various changes and modifications can be made without departing from the spirit and scope of the present invention. It therefore is the intent to encompass within the appended claims all such changes and modifications that fall within the scope of the present invention.

What is claimed is:

1. A syringe assembly for introducing fluids into the body of an animal and connectable with a catheter, said assembly comprising:

a syringe having a tubular body with an outwardly extending flange at one end, a piston slidably positioned in said body, a discharge extension, an intermediate portion connecting said tubular body and said discharge extension, said discharge extension including engagement means for engaging a connector thereto, and an outlet from said discharge extension;

a connector comprising a hollow tubular body having a first and second end and an intermediate portion defining the axial spacing between said first and second ends, said connector including first attachment means positioned internally on said first end and disposed for engaging said discharge extension engagement means, and second attachment means positioned internally on said second end and disposed for engaging said catheter; and said first attachment means designed to rotatably engage said discharge extension engagement means so as to permit purely rotational movement of said connector about said discharge extension and preclude translational movement thereon.

2. An assembly as defined in claim 1, wherein said discharge extension includes guide means for axially guiding said connector into position on said discharge extension.

3. An assembly as defined in claim 2, wherein said guide means includes a conically shaped portion of said discharge extension, the taper of said conically shaped portion extending outwardly from said engagement means toward said outlet so as to permit the gradual acceptance of the first attachment means of said connector as said connector traverses axially across said outlet toward said engagement means.

4. An assembly as defined in claim 3, wherein said engagement means comprises a track in said discharge extension, said track disposed adjacent to said conically shaped portion in the direction of said tubular body.

5. An assembly as defined in claim 4, wherein said first attachment means comprises first and second tabs, said tabs disposed opposite one another.

6. An assembly as defined in claim 5, wherein said second attachment means comprises a multiple start thread for engaging said catheter, thereby permitting attachment of said catheter by rotating said connector about said discharge extension causing said catheter to become threadly engaged with said connector so as to avoid twisting either said syringe or said catheter.

7. An assembly as defined in claim 6, wherein said intermediate portion includes window portions adjacent said first and second tabs to facilite rotational movement of said connector and increase flexibility of said intermediate portion.

8. A connector for securely interconnecting a catheter and a syringe, said connector comprising:
   a hollow tubular body having a first and second end and an intermediate portion defining the axial spacing between said first and second ends;
   said hollow tubular body including first attachment means positioned internally on said first end and disposed for engaging said syringe, and second attachment means positioned internally on said second end and disposed for engaging said catheter; and
   said first attachment means designed to rotatably engage said syringe so as to permit purely rotational movement of said connector about said syringe and preclude translational movement thereon.

9. A connector as defined in claim 8, wherein said first attachment means comprises first and second tabs, said tabs disposed opposite one another.

10. A connector as defined in claim 9, wherein said second attachment means comprises a multiple start thread for engaging said catheter, thereby permitting attachment of said catheter by rotating said connector about said syringe causing said catheter to become threadly engaged with said connector so as to avoid twisting either said syringe or said catheter.

11. A connector as defined in claim 10, wherein said intermediate portion includes window portions adjacent said first and second tabs to facilite rotational movement of said connector and increase flexibility of said intermediate portion.

12. An angiographic syringe for introducing fluids into the body of an animal for use in combination with a catheter and a syringe-catheter connector having a first attachment means for engaging with a syringe, said syringe comprising:
   a tubular body having an outwardly extending flange at one end;
   a piston slidably positioned in said body;
   a discharge extension;
   an intermediate portion connecting said tubular body and said discharge extension;
   said discharge extension including engagement means for engaging a connector thereto;
   an outlet from said discharge extension; and
   said engagement means designed such that said first attachment means of said connector rotatably engages therewith, thereby permitting only rotational movement of said connector about said discharge extension and precluding translational movement thereon.

13. A syringe as defined in claim 12, wherein said discharge extension includes guide means for axially guiding said connector into position on said discharge extension.

14. A syringe as defined in claim 13, wherein said guide means includes a conically shaped portion of said discharge extension, the taper of said conically shaped portion extending outwardly from said engagement means toward said outlet so as to permit the gradual acceptance of the first attachment means of said connector as said connector traverses axially across said outlet toward said engagement means.

15. A syringe as defined in claim 14, wherein said engagement means comprises a track in said discharge extension, said track disposed adjacent to said conically shaped portion in the direction of said tubular body.

16. A syringe assembly as defined in claim 1, wherein said hollow tubular body is of integral one-piece construction, said connector first attachment means is formed internally on said first end of said hollow tubular body and rotatably receives said discharge extension engagement means in said first end of said body, and said connector second attachment means is formed internally on said second end of said hollow tubular body for receiving a portion of said catheter in said second end of said body.

17. A connector as defined in claim 8, wherein said hollow tubular body is of integral one-piece construction, said first attachment means is formed internally on said first and of said hollow tubular body for receiving a portion of said syringe in said first end, and said second attachment means is formed internally on said second end of said hollow tubular body for receiving a portion of said catheter in said second end.

* * * * *